US009907455B2

(12) United States Patent
 Smith et al.

(10) Patent No.: US 9,907,455 B2
(45) Date of Patent: Mar. 6, 2018

(54) MEDICAL TOOLS AND RELATED METHODS OF USE

(71) Applicant: Boston Scientific Scimed, Inc., Maple Grove, MN (US)

(72) Inventors: Paul Smith, Smithfield, RI (US); Gary Kappel, Acton, MA (US); Naroun Suon, Lawrence, MA (US); Samuel Raybin, Marlborough, MA (US); Barry Weitzner, Acton, MA (US); Eric Tat, Canton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 371 days.

(21) Appl. No.: 14/177,960

(22) Filed: Feb. 11, 2014

(65) Prior Publication Data

US 2014/0228859 A1   Aug. 14, 2014

Related U.S. Application Data

(60) Provisional application No. 61/764,764, filed on Feb. 14, 2013.

(51) Int. Cl.
 *A61B 1/00* (2006.01)
 *A61B 1/018* (2006.01)
 (Continued)

(52) U.S. Cl.
 CPC ...... *A61B 1/00131* (2013.01); *A61B 1/00121* (2013.01); *A61B 1/00147* (2013.01);
 (Continued)

(58) Field of Classification Search
 CPC ............ A61B 1/00064; A61B 1/00066; A61B 1/00068; A61B 1/00121; A61B 1/00124;
 (Continued)

(56) References Cited

U.S. PATENT DOCUMENTS

| 2007/0167680 | A1* | 7/2007 | Miyamoto | ........... A61B 1/0055 600/106 |
| 2008/0188871 | A1* | 8/2008 | Smith | ................. A61B 1/0014 606/139 |

(Continued)

OTHER PUBLICATIONS

International Search Report in PCT/US2014/015830 dated Apr. 28, 2014 (4 pages).

*Primary Examiner* — Ryan Henderson
(74) *Attorney, Agent, or Firm* — Bookoff McAndrews, PLLC

(57) ABSTRACT

Medical systems are disclosed and may include an elongate member having a proximal end, a distal end, one or more channels extending between the proximal end and the distal end, and a handle operably coupled to the proximal end. The handle may include one or more ports in communication with the one or more channels. The medical systems may further include a docking station supporting the proximal end of the elongate member. The docking station may include a receiver adapted to receive and secure the handle and an adaptor guide unit having a distal end, a proximal end, and one or more passages formed therethrough, the one or more passages communicating with the one or more channels.

20 Claims, 4 Drawing Sheets

(51) Int. Cl.
A61B 5/00 (2006.01)
A61B 8/00 (2006.01)
A61B 90/50 (2016.01)
A61B 17/29 (2006.01)

(52) U.S. Cl.
CPC ............ *A61B 1/018* (2013.01); *A61B 5/6835* (2013.01); *A61B 8/4209* (2013.01); *A61B 90/50* (2016.02); *A61B 2017/2906* (2013.01)

(58) Field of Classification Search
CPC ............ A61B 1/00126; A61B 1/00128; A61B 1/00131; A61B 1/00133; A61B 1/0014; A61B 1/00147; A61B 1/00149; A61B 8/4209; A61B 50/20; A61B 5/6835; A61B 90/50; A61B 1/012; A61B 1/0125; A61B 1/018; A61B 2017/2906
USPC ....... 600/104, 106, 107, 127, 129, 156–159, 600/175; 606/1, 130, 205–209
See application file for complete search history.

(56) References Cited

U.S. PATENT DOCUMENTS

| | | | |
|---|---|---|---|
| 2009/0023985 A1* | 1/2009 | Ewers | A61B 1/00147 600/104 |
| 2010/0286478 A1 | 11/2010 | Ewers et al. | |
| 2011/0118545 A1* | 5/2011 | Williams | A61B 1/00052 600/104 |
| 2012/0118088 A1 | 5/2012 | Smith et al. | |
| 2012/0172850 A1 | 7/2012 | Kappel et al. | |

* cited by examiner

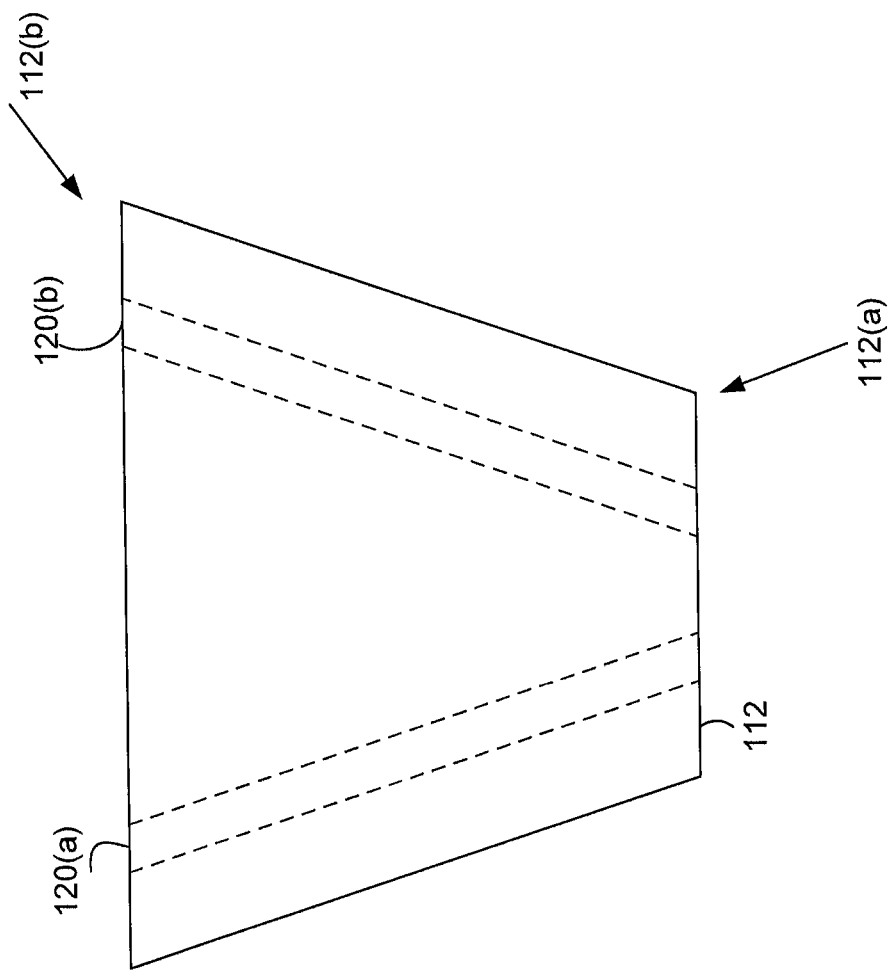

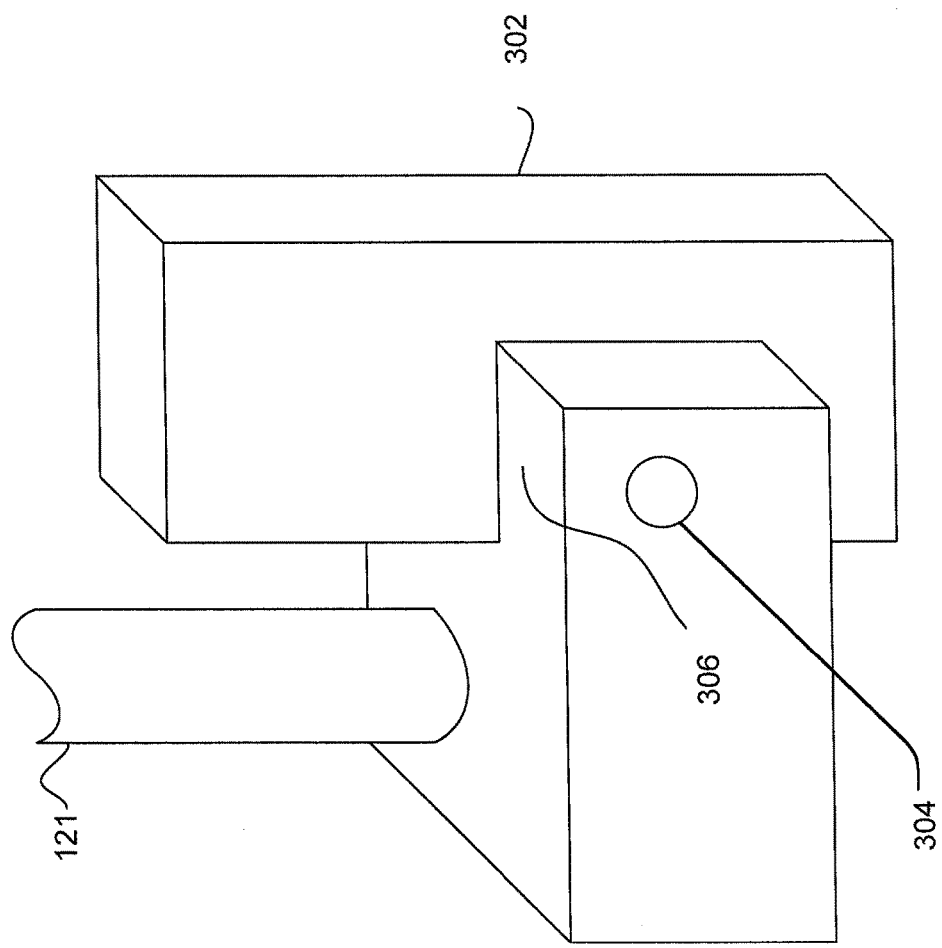

MEDICAL TOOLS AND RELATED METHODS OF USE

CROSS-REFERENCE TO RELATED APPLICATIONS

This application claims the benefit of priority from U.S. Provisional Application No. 61/764,764, filed on Feb. 14, 2013, the entirety of which is incorporated by reference herein.

FIELD OF THE DISCLOSURE

Embodiments of the present disclosure relate generally to medical devices suitable for use in medical procedures. In particular, embodiments of the instant disclosure relate to a docking station or stabilizing system for medical devices.

BACKGROUND

In the medical field, introduction sheaths, such as, e.g., endoscopes, are now widely used for diagnostic or therapeutic procedures of various diseases. Endoscopes generally take the form of a long, flexible tube, including a light conductor along with one or more channels for inserting various medical instruments. Typically, the endoscope is inserted into a patient's body through an incision or natural orifice. Within the body, these instruments allow for minimally invasive surgery, providing platforms for employing numerous tools, such as devices to grasp, clip, sever, and/or remove objects from inside the body, as well as devices to illuminate and view the surgical field.

Accurately positioning the tip of an endoscope at a precise location within a patient's body can pose a problem. Conventional instruments require considerable effort from large muscle groups such as wrists, elbows, and arms, and the manual effort required for moving the instruments from one site to another can be a factor during a given procedure. Moreover, the length and size of conventional equipment increases the complexity of the entire system. Indeed, two operators are often required; one for managing one Degree of Freedom (DoF) that defines various instruments' movements such as in/out, rotation, while another manages the endoscope and shaft of the tool. Additionally, the endoscopes are not capable of providing an angled approach or divergence to the instruments to direct the instrument toward a particular area inside the body. The existing systems do not allow physicians to manipulate the instruments inside the patient's body without a significant physical effort on the physician's part. Thus, a system that significantly reduces the physician's physical effort during a medical procedure is desirable.

SUMMARY

Embodiments of the present disclosure are directed towards a system for introducing finger controlled instruments into a patient's body.

A medical system may include an elongate member having a proximal end, a distal end, one or more channels extending between the proximal end and the distal end, and a handle operably coupled to the proximal end. The handle may include one or more ports in communication with the one or more channels. The medical system may further include a docking station supporting the proximal end of the elongate member. The docking station may include a receiver adapted to receive and secure the handle and an adaptor guide unit having a distal end, a proximal end, and one or more passages formed therethrough, the one or more passages communicating with the one or more channels.

Various embodiments of the medical system may include one or more of the following features: a support structure for securing the docking station to a location adjacent a patient; one or more medical instruments may be introduced through the passages and into the elongate member; the medical instruments may be operated by a small muscle group of a user; the adaptor guide unit may include two passages disposed at an angle relative to one another; the two passages of the adaptor guide unit may be in communication with two ports on the handle of the elongate member; the medical instruments may be configured to be operated by fingers of a user; the elongate member may be an endoscope; each of the medical instruments may include an end-effector, and the fingers of a user may control one of a position of the end-effector and a configuration of the end-effector; and each of the medical instruments may be steerable independently of the elongate member.

In another embodiment, a stabilizing system for controlling medical instruments positioned inside the body of a patient may include a docking station supporting a proximal end of an elongate member. The docking station may include a receiver adapted to receive and secure a handle portion of the elongate member, a adaptor guide unit having a distal end, a proximal end, and one or more passages formed lengthwise therethrough, and a securing mechanism configured to secure the docking station at a position adjacent the patient.

Various embodiments of the stabilizing system may include one or more of the following features: the elongate member may include a plurality of working channels in communication with the one or more passages formed in the adaptor guide unit; at least one medical instrument may be disposed in one of the plurality of channels; the at least one medical instrument may include an end-effector, and the fingers of a user control one of a position of the end-effector and a configuration of the end-effector; the elongate member may include a handle having at least one port in communication with at least one of the passages formed in the adaptor guide unit; the at least one medical instrument may be steerable independently of the elongate member; the at least one medical device may be configured to be operated by fingers of a user; the adaptor guide unit may include two passages disposed at an angle relative to one another.

In another embodiment, a method for operating a medical device may include securing a handle of an endoscope in a docking station, wherein the endoscope includes a plurality of working channels, wherein the docking station comprises a adaptor guide unit having passages in communication with the working channels, and wherein the docking station is secured to a position adjacent a user. The method may also include introducing one or more medical devices into the passages and working channels, wherein the one or more medical devices include medical devices configured for operation by fingers of a user. The method may further include performing a medical procedure by manipulating the one or more medical devices. In some embodiments, the adaptor guide unit may include two passages disposed at an angle relative to one another.

It is to be understood that both the foregoing general description and the following detailed description are exemplary and explanatory only, and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 2 is a detail plan view of an adaptor guide unit for use with the system of FIG. 1

FIG. 3 is a detail pictorial view of a leg member clamp mechanism.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to medical devices used to introduce and manipulate instruments employed in minimally-invasive surgery, typically involving an endoscope or other suitable introduction sheath. More particularly, embodiments of the disclosure provide a stabilizing system for maintaining the proximal end of an endoscope in a steady, stable position during a surgical procedure. Thus, the medical devices are more accurately manipulated with less energy being expended by the operator or physician. The stabilizing system further allows the operator to manipulate instruments more precisely and with less effort, using small muscle groups such as in the fingers and hands. Thus, instruments that may be operated with small muscle groups reduce stress, and allow for a smaller and lighter design that can be manufactured at lower cost. The stabilizing system broadly comprises an elongate introduction sheath, such as an endoscope, secured in a stable position by a docking station. The elongate introduction sheath includes a handle and one or more working channels, accessible via ports in the handle. The docking station generally includes a receiver, adapted to receive and secure the elongate member handle; a adaptor guide unit, which facilitates introduction of medical devices into working channels of the elongate members, through passages formed in the adaptor guide unit; and a leg member, which clamps the docking station to an object (e.g., a patient's bed), to fixedly secure the docket station proximate the patient.

Figure 1:
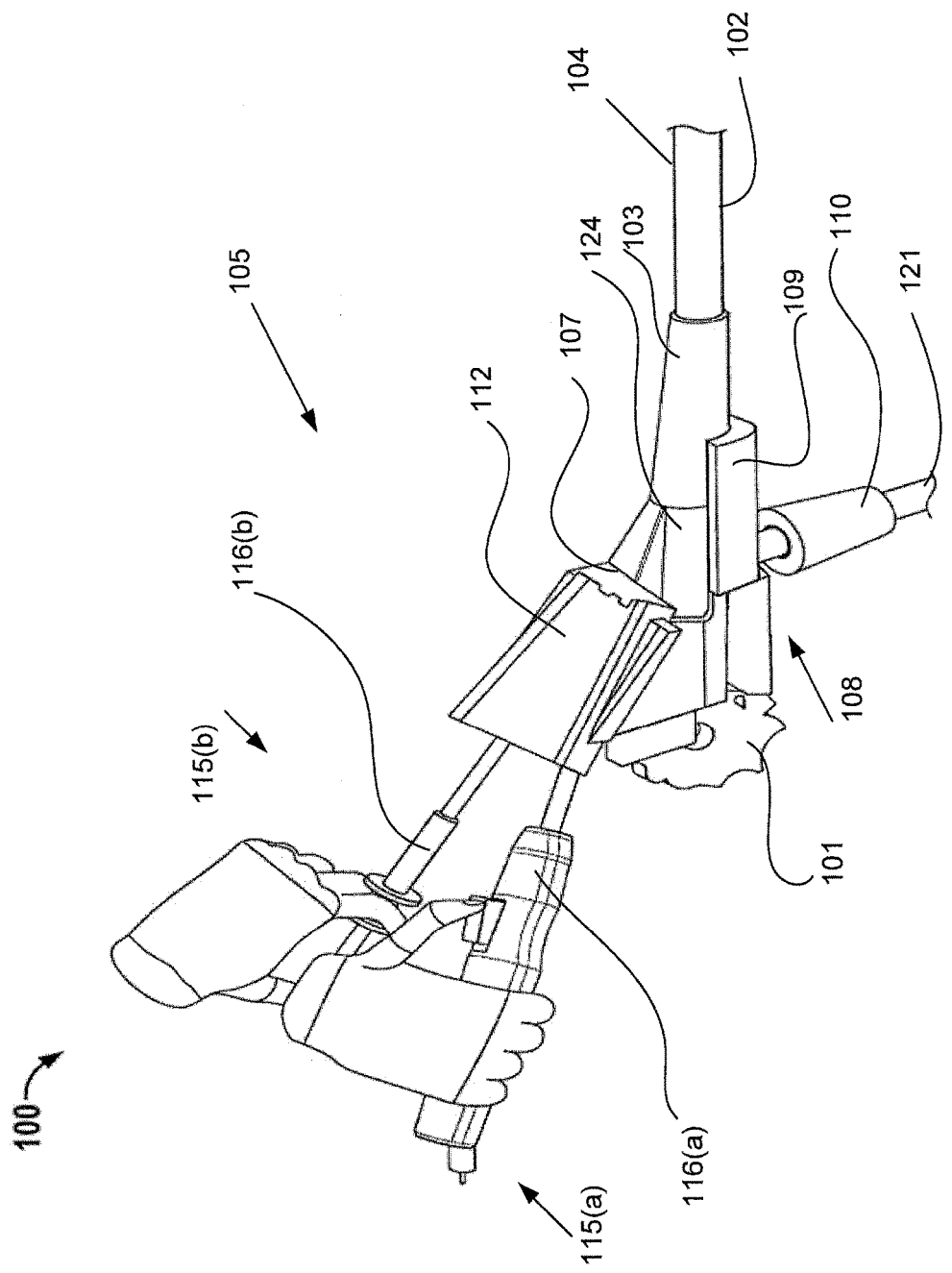
FIG. 1 is a perspective view of an overall system, according to embodiments of the present disclosure.

FIG. 1 illustrates an exemplary stabilizing system 100 according to embodiments of the present disclosure. The stabilizing system 100 includes an elongate member 102, which can be a conventional endoscope or endoscopic device, having a proximal end 104, a distal end (not shown), and one or more channels (not shown) extending between the proximal end 104 and the distal end (not shown). As will be appreciated from the discussion below, elongate member 102 may be a double-channel endoscope. The elongate member 102 also includes a handle 103. The handle 103 can provide, for example, control knobs 101 for manipulating the distal tip of the elongate member 102 during insertion into a patient. Handle 103 may include one or more ports 107, which provide ready access to the channels of the elongate member 102. One port may be provided for each available channel in the elongate member 102. Alternatively, a single port may provide access to all of the channels within the elongate member 102. Various embodiments of the present disclosure may employ various forms of endoscopic devices, adapted for particular surgical procedures. For example, a procedure involving the small intestine may call for a duodenoscope. Those of skill in the art will recognize that other suitable endoscopic instruments may be used, as needed. Such instruments may be selected in needed configurations, diameters, or shapes. Medical devices to be employed in using embodiments of the present disclosure are discussed in more detail below.

The stabilizing system 100 may further include a docking station 105 that secures the elongate member 102 in a stable position adjacent the patient. The docking station 105 includes a receiver 108 that receives and secures the elongate member handle 103, an adaptor guide unit 112, and a leg member 110. As explained below, the adaptor guide unit 112 facilitates insertion of medical devices into the elongate member working channels, and the leg member 110 supports the receiver 108 and secures it to a stationary object, such as, e.g., a patient's bed.

The elongate member 102 may comprise an endoscope, for example, and may carry any number of medical instruments via the proximal end 104 of the elongate member 102, to a location within a patient's body for surgery, treatment, and/or diagnosis. The elongate member 102 may be of any suitable length, such as, but not limited to, 100 cm, 160 cm, or 240 cm. The elongate member 102 may further include an end-effector (as shown in, e.g., FIG. 4A) extending distally therefrom. Other exemplary tools that may be carried at the distal tip of elongate member 102 may include a light source, a camera or other suitable imaging devices, and other devices for visualizing the surgical field. The elongate member 102 may include one or more channels for inserting medical instruments. The medical instruments may allow the physician to perform fine tissue manipulation using small muscle groups, such as muscles in the fingers and/or thumb. The medical instruments may be steerable independently of elongate member 102.

According to an embodiment, different medical instruments may be inserted into different endoscope channels. For example, an operator may place a cutting tool in one channel, and a retraction tool in another channel. It is understood that other exemplary instruments may be inserted in the working channels without departing from the scope of the present disclosure. Some channels may have a larger diameter, while others may have a smaller diameter. Further, some channels may include permanently fixed devices, such as light sources or cameras, while other channels may allow temporary insertion of medical instruments, as the operator may desire. Various examples of medical instruments that may be resident in any one of the channels include, but are not limited to, suction pumps, cauterization instruments, graspers, clippers, lasers, baskets, lithotripters, forceps, biopsy devices, tissue removal instruments, and tissue cutting instruments. These medical instruments may allow operators/physicians to perform procedures within the patient's body. In one example, the medical instruments may extend beyond the working channel of the elongate member 102, e.g., be about 8 inches longer than the working channel, depending on the particular medical procedure. Alternatively, the length of the medical instruments may vary based on the configuration of the elongate member 102.

Receiver 108 is adapted to receive and secure handle 103 of elongate member 102. It will be understood, therefore, that the exact configuration of receiver 108 may depend on the configuration of the handle 103 employed in a particular application. The following discussion provides sufficient information for those in the art to configure a receiver 108 for a given circumstance. The illustrated embodiment in FIG. 1 includes a receiver flange 109, which may be a channel-shaped device dimensioned to receive a portion of handle 103, and a fastening means (not shown) for fixing the handle 103 in position. The channel may be formed in, e.g., a U-shaped or L-shaped form, or other suitable form as desired, receiving the handle 103 on its flat bottom and securing the handle 103 against at least one upright side portion. The fastening means can be any suitable fastener, such as a set screw, spring mount or the like, having sufficient retentive capability to resist the forces likely to be applied to the handle 103. The receiver 108 may be formed from a material suitable for a surgical environment, such as stainless steel or a polymer material.

Adaptor guide unit 112 is a generally plate-like device, positioned in abutment with the ports 107 and extending generally at a shallow angle to and away from handle 103. Adaptor guide unit 112 extends the angle of the introduction port (not shown) of the elongate member 102 to provide enough space on the proximal end 104. Thus, the adaptor guide unit 112 may help in elongating medical tools interface with working channels of the elongate member 102. As shown in detail in FIG. 2, the adaptor guide unit 112 may take the form of a trapezoid, its distal end 112(a) being generally more narrow end than proximal end 112(b). Adaptor guide unit 112 can be fixed to the receiver 108, integral with docking station 105, dimensioned and positioned so that the handle 103 slides into receiver flange 109 until the ports 107 fit against the adaptor guide unit distal end 112(a), at which time the handle 103 is fixed in position within receiver flange 109. Alternatively, adaptor guide unit 112 may be mounted directly on handle 103, employing a suitable mounting structure. The desirability of a trapezoidal form for adaptor guide unit 112 will be explained more fully below. Alternative shapes may be selected for adaptor guide unit 112, in keeping with particular requirements for a given application.

With continuing reference to FIG. 2, passages or channel extensions 120(a) and 120(b) run lengthwise through adaptor guide unit 112, from its distal end 112(a) to its proximal end 112(b). These passages may be sized generally similarly or identically to the ports 107, designed to pass a medical device from the adaptor guide unit proximal end 112(b), through the adaptor guide unit 112, into ports 107, and then into the working channels of the elongate member 102. Passages 120(a) and 120(b) run generally parallel to the sides of adaptor guide unit 112, so that the proximal ends of the channels are spaced farther apart than are the distal ends. In practice, the spacing and alignment of the passages 120 can be adjusted as desired. In one embodiment, for example, the passages 120(a) and 120(b) may be located as little as 1 inch distant from the point of entry (introduction port) of the elongate member 102. The cross-sectional diameter of the passages 120(a) and 120(b) may maintain minimal bearing diameter that does not exceed the working channel diameter of the elongate member 102. The passages 120(a) and 120(b) may have a divergence configuration that allows forces to be applied downwardly to the medical instruments. Advantages of the embodiment depicted in FIG. 2 will be set out more fully, below.

The medical systems and stabilizing systems presently disclosed may comprise biocompatible materials. For example, the passages and/or channels may be made from a variety of suitable biocompatible materials such as nitinol, stainless steel, or polyimide. The chosen material may be based on desired stiffness, resilience, and/or other properties, as will be understood to those skilled in the art. The passages and/or channels may be coated with a suitable friction reducing material such as, e.g., TEFLON®, polyetheretherketone, polyimide, nylon, polyethylene, or other lubricious polymer coatings. Such coatings may, for example, reduce surface friction with the surrounding tissues.

Referring to FIG. 1, receiver 108 is supported by leg member 110, extending downward from the bottom of receiver flange 109. The receiver 108 is joined to the leg member 110 by mounting attachment 124, which may provide one or more degrees of freedom for adjusting the alignment and position of the docking station 105. First, mounting attachment 124 may rotate, allowing receiver 108 to rotate in a horizontal plane. Also, or alternatively, mounting attachment 124 may pivot about an axis perpendicular to leg member 110, allowing the distal end of handle 103 to pivot up or down, as desired. Finally, attachment 124 may be provided with a sliding extension, allowing the docking station 105 to be shifted up and down. Mounting attachment 124 may also be fitted with a locking device, so that each of the adjustments may be fixed in place. A person of ordinary skill in the art will recognize further variations of attachment 124 suitable for the present disclosure.

Leg member 110 includes a clamp mechanism 121, fixed to the end of leg member 110 and clamped to a suitable object 302 as shown in FIG. 3. It will be understood that any suitable clamping or attachment mechanisms may be employed according to a particular application. The clamp shown in the illustrated embodiment includes side extensions 306, chosen to fit around a desired object 302 (such as, e.g., a portion of the patient's bed), and a set screw arrangement 304, adapted to fix the clamping mechanism to the object 302. It will be understood that object 302 should be chosen with a view to sufficiently support docking station 105, elongate member 102, and/or any associated medical devices as set out below. A portion of a table, or a table leg, might comprise suitable objects, for example.

FIG. 1 shows the stabilization system 100 of the present disclosure in use. Prior to use, docking station 105 is mounted, with a clamp mechanism 121 securely attached to an object 302 (as shown in, e.g., FIG. 3). Also, the adjustable settings of adjustment mechanism will be positioned as desired to most effectively position elongate member 102 with respect to the patient. Then, elongate member 102 may be slid into place on receiver flange 109 and also fixed in place. When ready, the distal end of elongate member 102 is inserted into a patient, and its distal tip maneuvered to the surgical site within the patient.

At that point, medical devices such as devices 115(a) and 115(b) may be employed as shown in FIG. 1. In one embodiment, for example, the medical devices 115(a) and/or 115(b) may be limited to sweep in one plane. The illustrated devices 115(a) and 115(b) may be similar to endoscopic medical devices and suitable for employment within working channels of an endoscope. As shown, each medical device 115(a) and 115(b) includes its own control handle 116(a) and 116(b), respectively, and elongated portion (such as, e.g., an elongated shaft) extending therefrom. Each device is employed by inserting its distal tip the into a channel extension 120(a) or 120(b), through the adaptor guide unit 112, and into the ports 107, onward through a working channel of the elongated member 102, exiting from that member at the surgical site. A single medical device may be employed, or the number of medical devices may be increased up to the number of available working channels of the elongate member 102, ports 107, and channel extensions, e.g, 120(*a*) and 120(*b*). In addition, in some embodiments, a plurality of medical devices may be deployed in a single working channel. In some scenarios, the stabilizing system 100 enhances the functionality of medical devices 115(*a*) and 115(*b*) for positioning within the body.

The distal tip of each medical device 115(*a*) and 115(*b*) may include any suitable endoscopic end-effectors to a given treatment site in the patient. An example of a suitable medical device is the tissue grasper 400 shown in FIG. 4A, which depicts grasper 400 in an open configuration. The tissue grasper 400 may be passed through a lumen of the elongated member 102, and it includes an end-effector 401 extending distally from a flexible shaft 408, which may be disposed within the elongated member 102. The flexible shaft 408 may include an actuation member or control member (not shown) therein. The control member extends through the flexible shaft 408 translating the movements from a controller or handle 116 present at the proximal end 104 (see, e.g., FIG. 1) of the flexible shaft 408. The flexible shaft 408 may also include a clevis member 407 or other suitable fastener system that is present at its distal end.

Figure 4A:
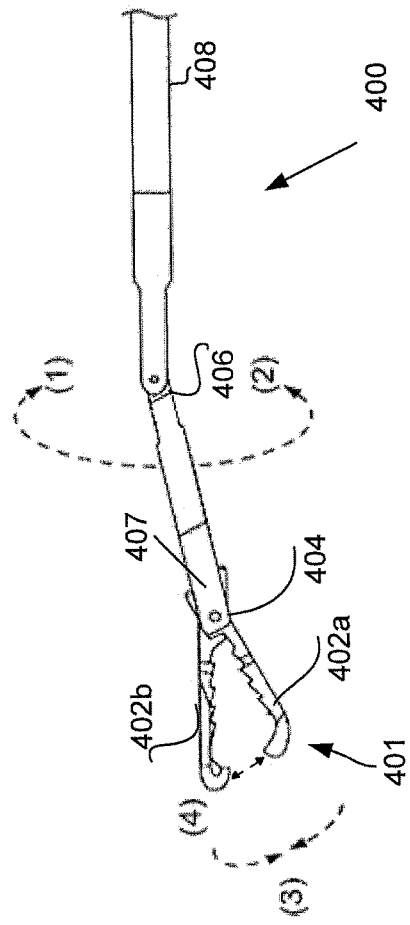
FIGS. 4A and 4B depict an end-effector (embodied here as a grasper) and a control handle, respectively, for use with the system of FIG. 1.

The end-effector 401 includes two jaws or arms, an upper arm 402*b* and a lower arm 402*a*, (hereafter, arms 402) pivotally connected to each other. The arms 402 may be pivotably coupled to the clevis 404 of clevis member 407 via a pivot pin. A proximal end 406 of arms 402 may be rotatably connected to flexible shaft 408 at a pivot point to permit arms 402 to rotate about the pivot as shown in FIG. 4*a*. A control member (not shown) may be operably connected to the proximal end 406 of one or both of arms 402, so that actuating the arms 402 at their proximal end 406 translates into movement of the arms 402 at their distal end. While both arms 402 may be pivotable relative to one another, in some embodiments, one of the arms (e.g., 402*a*) may be fixed, and the other arm (e.g., 402*b*) be movable, so the control member actuates only the movable arm (402*b*). Once the one or more end-effectors are in position at the surgical site, the operator can control the end-effectors by exerting a minimum of force.

Figure 4B:
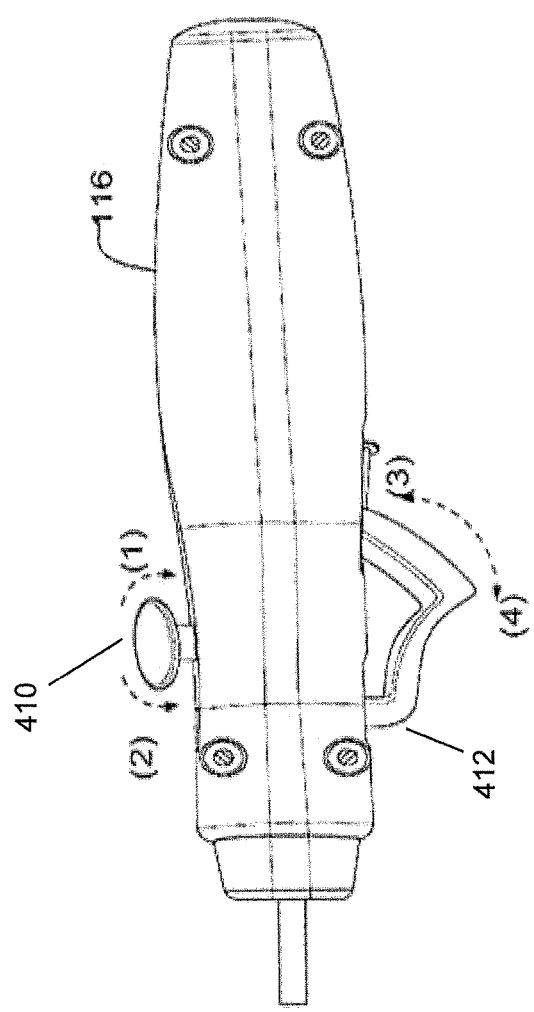

In one embodiment, the devices used with stabilizing system 100 may include one or more control handles, e.g., 116(*a*) and 116(*b*). The control handles 116 as shown in FIG. 4B belong to tools inserted through the channels 120(*a*) and 120(*b*), respectively, and into the elongate member 102, thus, facilitating fine manipulation of the tools inside the body. Small muscle groups such as muscles of the fingers, thumb, and/or wrists, may be used to operate the control handle 116, which also may be extended through the channel extensions 120(*a*) and 120(*b*) shown in FIG. 2. The control handle 116 may include a mechanism for articulating or actuating a surgical tool at the distal end of the flexible shaft 408. The mechanism may include one or more buttons, triggers, or any other mechanisms suitable for manipulating the tools inside the body. According to an embodiment, the buttons, triggers or other mechanisms may provide one or more Degrees of Freedom (DoF) including, but not limited to, longitudinal movement (e.g., in/out), rotation, one-directional steering, and open/close.

FIGS. 4A and 4B depict the interaction between control handle 116 and the end-effector 401. A thumb-actuated lever 410 may be placed on the control handle 116. As shown, the forces exerted in pulling proximally (1) or pushing distally (2) move the grasper 400 upward or downward, respectively. Moreover, the control handle 116 may include a trigger 412 that may be used for performing actions such as closing or opening the grasper 400. The trigger 412 may perform the desired action via a single finger or the thumb. For example, pulling the trigger 412 (in direction of arrow (3)) may close the end-effector, e.g., grasper 401. Opening the grasper 401 may be performed by releasing the trigger 412 (in direction of arrow (4)).

From the description in connection with FIGS. 4A and 4B, together with consideration of FIG. 1, showing simultaneous operation of medical devices 115(*a*) and 115(*b*), it will be appreciated that providing extension channels 120(*a*) and 120(*b*) in a divergent configuration—that is, having their proximal ends spaced wider than their distal ends—may offer considerable advantage in operation, allowing the operator greater freedom in handling and moving the respective control handles 116(*a*) and 116(*b*).

The stabilizing systems disclosed herein may be used with single and/or multi-working channel scopes, including endoscopes that are commercially available.

The medical system of the present disclosure may provide simple, finger controlled medical instruments, thus downsizing and/or simplifying the supporting structure for the instruments. Accordingly, the system may reduce loads to be applied to the instruments, e.g., the amount of force that must be supplied to control the instruments, require less stabilization of the docking station, allow for use of more delicate instruments, and eliminate or decrease the complexity of rails and bearings.

Those skilled in the art will recognize that the present disclosure may be manifested in a variety of forms other than the specific embodiments described herein. Accordingly, departure in form and/or detail may be made without departing from the scope and spirit of the present disclosure as described in the appended claims.

What is claimed is:

1. A medical system, comprising:
   a member having a proximal end, a distal end, one or more channels extending between the proximal end and the distal end, and a handle operably coupled to the proximal end, the handle including one or more ports in communication with the one or more channels; and
   a docking station separable from the member and configured to support the handle, the docking station including:
      a receiver having a U-shaped receiver channel dimensioned to slidably and releasably receive a bottom surface of the handle and to releasably secure the handle to the docking station; and
      an adaptor guide unit defining an enclosed housing and having a distal end, a proximal end, and two or more passages extending therethrough from the proximal end to the distal end, wherein the adaptor guide unit is fixed relative to the receiver,
      wherein the adaptor guide unit is positioned relative to the receiver so that when the bottom surface of the handle is received within the receiver channel, the adaptor guide unit aligns with an upper surface of the handle, and the two or more passages are in communication with the one or more ports and the one or more channels enabling an instrument to extend through a passage of the two or more passages and into a channel of the one or more channels of the member.

2. The medical system of claim 1, further comprising a support structure for securing the docking station to a location adjacent a patient.

3. The medical system of claim 1, further comprising one or more medical instruments inserted through at least one of the two or more passages and into the member.

4. The medical system of claim 1, wherein two passages of the two or more passages are disposed at an angle relative to one another.

5. The medical system of claim 4, wherein the two passages of the adaptor guide unit are in communication with two ports on the handle of the member when the handle is received within the receiver channel so that a first of the two passages communicates with a first of the two ports, and a second of the two passages communicates with a second of the two ports.

6. The medical system of claim 3, wherein the medical instruments are configured to be operated by fingers of a user.

7. The medical system of claim 1, wherein the member is an insertion tube of an endoscope, and the handle is a handle of the endoscope.

8. The medical system of claim 7, wherein each of the medical instruments includes an end-effector, and each of the medical instruments is designed to be operated by one or more fingers of a user to control at least one of a position of the end-effector and a configuration of the end-effector.

9. The medical system of claim 1, wherein each of the medical instruments is steerable independently of the member.

10. The medical system of claim 1, wherein the receiver channel is configured so that the member is slideable within the receiver channel.

11. A stabilizing system for medical instruments, the stabilizing system comprising:
a docking station configured to support a handle portion of a member and being separable from the member, the docking station including:
a receiver having a U-shaped receiver channel dimensioned to slidably and releasably receive a bottom surface of the handle portion and to releasably secure the handle portion of the member to the docking station;
an adaptor guide unit defining an enclosed housing and having a distal end, a proximal end, and two or more passages extending lengthwise therethrough from the proximal end to the distal end, wherein the adaptor guide unit is fixed relative to the receiver, and wherein the adaptor guide unit is positioned relative to the receiver so that when the bottom surface of the handle is received within the receiver channel, the adaptor guide unit aligns with an upper surface of the handle enabling an instrument to extend through a passage of the two or more passages and into a working channel of the member; and
a securing mechanism configured to secure the docking station at a position adjacent to a patient.

12. The stabilizing system of claim 11, wherein the member includes a plurality of working channels in communication with the two or more passages extending in the adaptor guide unit when the handle of the member is received within the receiver channel.

13. The stabilizing system of claim 12, further comprising at least one medical instrument disposed in one of the plurality of working channels.

14. The stabilizing system of claim 13, wherein the at least one medical instrument includes an end-effector adapted for control by one or more fingers of a user to control at least one of a position and a configuration of the end-effector.

15. The stabilizing system of claim 11, wherein the handle has at least one port in communication with the two or more passages extending in the adaptor guide unit when the handle of the member is received within the receiver channel.

16. The stabilizing system of claim 13, wherein the at least one medical instrument is steerable independently of the member.

17. The stabilizing system of claim 13, wherein the at least one medical instrument is configured to be operated by fingers of a user.

18. The stabilizing system of claim 11, wherein two passages of the two or more passages are disposed at an angle relative to one another.

19. A method for operating a medical device, the method comprising:
securing a bottom portion of an endoscope handle in a U-shaped receiver channel located on a receiver of a docking station by sliding the handle into the receiver channel so that the docking station supports a proximal end of the endoscope, wherein the endoscope is separable from the docking station, wherein the endoscope includes a plurality of working channels, wherein the docking station comprises an adaptor guide unit fixed relative to the receiver, the adapter guide unit defining an enclosed housing and having a distal end, a proximal end, and passages extending therethrough from the proximal end to the distal end, and wherein securing the handle aligns distal ends of the passages with an upper portion of the handle so that the passages are in communication with the working channels when the handle is secured to the receiver, enabling the medical device to extend through at least one of the passages and into at least one of the working channels of the member, and wherein the docking station is secured to a position adjacent a patient;
introducing one or more medical devices into the at least one of the passages and the at least one of the working channels, wherein the one or more medical devices are configured for operation by fingers of a user; and
performing a medical procedure by manipulating the one or more medical devices.

20. The method of claim 19, wherein the adaptor guide unit includes two passages disposed at an angle relative to one another.

* * * * *